United States Patent [19]

Fanta

[11] 4,053,629

[45] Oct. 11, 1977

[54] INSECTICIDAL METHOD UTILIZING CERTAIN COUMARANOL ESTERS OF CYCLOPROPANE CARBOXYLIC ACIDS

[75] Inventor: Wayne I. Fanta, Colerain Township, Hamilton County, Ohio

[73] Assignee: The Procter & Gamble Company, Cincinnati, Ohio

[21] Appl. No.: 700,425

[22] Filed: June 28, 1976

Related U.S. Application Data

[63] and a continuation-in-part of Ser. No. 208,040, Dec. 9, 1971, Pat. No. 3,976,663, which is a continuation-in-part of Ser. No. 2,443, Jan. 12, 1970, abandoned.

[51] Int. Cl.$^2$ ............................................. A01N 9/28
[52] U.S. Cl. ................................................... 424/285
[58] Field of Search ......................................... 424/285

[56] References Cited

U.S. PATENT DOCUMENTS

| | | | |
|---|---|---|---|
| 3,414,607 | 12/1968 | Fujimoto et al. | 260/468 |
| 3,440,245 | 4/1969 | Kato et al. | 260/281 |
| 3,796,730 | 3/1974 | Katsuda et al. | 260/347.4 |

*Primary Examiner*—Allen J. Robinson
*Attorney, Agent, or Firm*—Ronald L. Hemingway; Jack D. Schaeffer; Richard D. Witte

[57] ABSTRACT

Cyclopropanecarboxylic acid esters of 3-coumaranol and substituted 3-coumaranols possessing useful insecticidal properties.

5 Claims, No Drawings

INSECTICIDAL METHOD UTILIZING CERTAIN COUMARANOL ESTERS OF CYCLOPROPANE CARBOXYLIC ACIDS

CROSS REFERENCE TO RELATED APPLICATIONS

This application is a division of application Ser. No. 208,040, filed December 9, 1971 (now U.S. Pat. No. 3,976,663, issued Aug. 24, 1970), which is a continuation-in-part of application Ser. No. 2,443, filed Jan. 12, 1970, now abandoned.

BACKGROUND OF THE INVENTION

This invention relates to novel cyclopropanecarboxylic acid esters of 3-coumaranol, and derivatives thereof, as well as insecticidal compositions containing said esters as an essential active ingredient.

Current trends in the chemical control of insects call for inherently safer materials which degrade very rapidly to non-toxic substances once their purpose is accomplished. The safety of the widely used chlorinated hydrocarbons, notably DDT, is currently under question largely because of their poor biodegradability and concomitant persistence. Accordingly, there is a great demand for alternative broad spectrum insecticides which are suitable for the high volume usage entailed in agricultural applications. At the same time it is desirable for new insecticides to exhibit a low order of toxicity to warm-blooded animals. Of the several insecticidal classes which demonstrate low mammalian toxicity and good biodegradability, it has long been recognized that pyrethrum, a naturally-occurring insecticidal mixture, possesses these desirable properties. In addition to the safety advantages, this natural mixture causes rapid knock-down and kill of a broad spectrum of insects; however, it is unstable to light, air, and heat, and is very expensive. The most active component of pyrethrum is pyrethrin I and number of analogous compounds have been proposed for insecticidal use. Allethrim, a typical synthetic pyrethrin-like insecticide, while more stable to light and heat than pyrethrum, is nevertheless expensive, a defect which is compounded by the fact that this substance is not appreciably synergized by the low cost synergizing agents such as piperonyl butoxide which are typically used in insecticidal compositions. Because of instability, high cost and limited supply, the use of pyrethrum and pyrethrin-like insecticides in agricultural applications has been precluded or seriously limited.

At the same time, it is well known that certain insects, in time, become immune to the insecticidal properties of various chemical agents. To be efficient, an insecticide should be able to resist detoxification by the insect. While biological mechanisms whereby insects are capable of detoxifying the various types of insecticidal compounds are not fully understood, it is possible that, as with other biological systems, insects may in time develop new biochemical processes capable of detoxifying any particular insecticidal compound. In any event, it is desirable to have included in the insecticidal armamentarium compounds which can be utilized once a given class of insects is found no longer to respond to conventional insecticidal compounds.

Many prior art insecticidal esters differ from one another and from the natural pyrethrin I esters by virtue of synthetic modifications in the alcohol moiety of the ester. Other synthetic insecticides are pyrethrin-like esters modified in the acid portion of the ester molecule. For example, the applications of Fanta, entitled "INSECTICIDAL ESTERS OF 3-(2,2-TETRAMETHYLENE ETHENYL)-2,2-DIMETHYLCYCLOPROPANECARBOXYLIC ACID," Ser. No. 23,513, filed Mar. 17, 1970 (now U.S. Pat. No. 3,679,667, issued July 25, 1972); NOVEL ESTERS OF CHRYSANTHEMIC ACID", Ser. No. 2,443, filed Jan. 12, 1970 (now abandoned); the copending application of Crawford, entitled "INSECTICIDAL ESTERS OF 1-ACENAPHTHENOL", Ser. No. 198,434, filed Nov. 12, 1971, and now U.S. Pat. No. 3,840,584, issued Oct. 8, 1974; and U.S. Pat. No. 3,465,007, Sept. 2, 1969, to M. Elliott, all relate to various synthetic insecticidal esters of the pyrethrum type. It has now been discovered that 3-coumaranol, and the various derivatives thereof, can be used in conjunction with cyclopropanecarboxylic acids to provide insecticidal esters of the pyrethrum type.

It is therefore an object of this invention to provide novel insecticidal 3-coumaranol esters of cyclopropanecarboxylic acids which are biodegradable, effect rapid knock-down and kill of a broad spectrum of insects, possess low mammalian toxicity and are less susceptible to detoxification by insects than is pyrethrum. This and other objects are obtained by the present invention as will become apparent from the following disclosure.

SUMMARY OF THE INVENTION

The novel compounds of the present invention include certain cyclopropanecarboxylic acid esters of 3-coumaranol and substituted derivatives of 3-coumaranol. (The "3-coumaranol" compounds may be alternatively named as derivatives of 2,3-dihydro-3-benzofuryl compounds; the "chrysanthemic acid" esters herein can also be named as derivatives of 2,2-dimethyl-3-(2-methylpropenyl)cyclopropanecarboxylic acid.)

This invention also encompasses insecticidal compositions comprising as an essential ingredient an insecticidal amount of certain cyclopropanecarboxylic acid esters of 3-coumaranol or a substituted 3-coumaranol.

As a method aspect, the present invention encompasses a method of combatting insects comprising applying an insecticidal amount of a cyclopropanecarboxylic acid ester of 3-coumaranol or substituted 3-coumaranol to an insect or insect habitat.

DETAILED DESCRIPTION OF THE INVENTION

The cyclopropanecarboxylic acid esters of 3-coumaranol, and derivatives of 3-coumaranol are of the formula

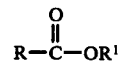

wherein R is a cyclopropane moiety selected from the group consisting of

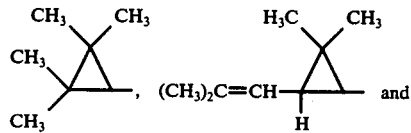

-continued

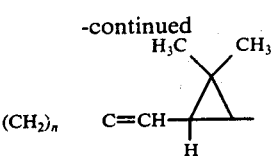

wherein n is an integer of from 4 to 6, preferably 4, and wherein R¹ is a 3-coumaranyl moiety of the formula

wherein R² is selected from the group consisting of hydrogen, halogen, nitro, thiomethyl, alkyl (e.g., ethyl, methyl, propyl, butyl, neopentyl, isopropyl,), alkoxyl (e.g., methoxyl, ethoxyl), sulfonylmethyl, phenyl, benzyl, and the like. The esterification is at the 3-position on the coumaranol ring system.

The insecticidal compounds of this invention are prepared by esterifying 3-coumaranol and substituted derivatives thereof, with cyclopropanecarboxylic acids or acid halides in the manner hereinafter detailed. First, the 3-coumaranol compound is prepared by reacting salicylaldehyde or a 5-substituted salicylaldehyde with dimethyloxosulfonium methylide to secure the corresponding 3-coumaranol in accordance with the method described by B. Holt and P. A. Lowe, *Tetrahedron Letters*, No. 7, 683 (1966) as detailed by E. J. Corey and M. Chaykovski, *J. Amer. Chem. Soc.*, 87, 1353 (1965). The reaction proceeds as follows:

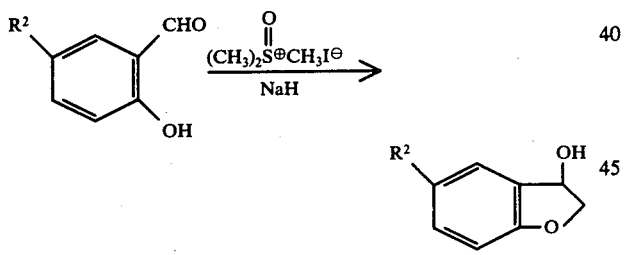

wherein R² is as above. Following this, the 3-coumaranol compound is esterified, e.g., by means of a cyclopropanecarboxylic acid halide, as follows:

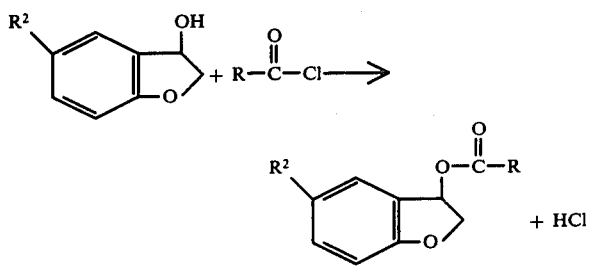

wherein R is as disclosed above.

According to the above outline, the esters of this invention are prepared by a step-wise process comprising: (1) preparing the 3-coumaranol compound according to the procedures described in the foregoing references; (2) esterifying the alcohol with a stoichiometric amount of a cyclopropanecarboxylic acid chloride which is also prepared by standard procedures (below).

Alternatively, the esterification step of the present invention can be effected in other ways. The 3-coumaranol compound can be heated with the appropriate cyclopropanecarboxylic acid in the presence of a strong acid (e.g., $H_2SO_4$, $HClO_4$, etc.) in an organic solvent capable of azeotropically boiling with water, thereby removing the water formed in the esterification. THe 3-coumaranol compound can also be heated with a lower alkyl ester of a cyclopropanecarboxyic acid in the presence of a basic catalyst such as sodium hydroxide, potassium hydroxide, sodium alcoholate or potassium alcoholate, and the like, while continuously removing the lower alcohol formed through transesterification of the reaction system. In such cases, the methyl, ethyl, n-propyl and iso-propyl esters of the cyclopropanecarboxylic acids are suitable. In the most preferable esterification, the 3-coumaranol compound is allowed to react with a cyclopropanecarboxylic acid halide, preferably at temperatures from about 20° C to about 100° C, in an inert solvent, preferably in the presence of an agent such as pyridine, triethylamine or other suitable amine, such that the esterification proceeds with the formation of a hydrohalic acid salt within a short period of time. For this purpose, the cyclopropanecarboxylic acid chloride is the most preferred, although the acid bromide and the acid iodide can be employed.

The cyclopropane carboxylic acids used to prepare the insecticidal esters of the instant invention can be prepared by standard procedures disclosed in the art. U.S. Pat. No. 3,679,667, July 25, 1972, to W. J. Fanta, above, describes the preparation of 3-(2,2-tetramethylene ethenyl)-2,2-dimethylcyclopropanecarboxylic acid; chrysanthemoyl chloride can be prepared in the manner of Crombie, et al., *J. Chem. Soc.* 3552 (1950); 2,2,3,3-tetramethylcyclopropanecarboxylic acid can be prepared in the manner of Matsui and Kitahara, *Agr. Biol. Chem.* (Tokyo) 31, 1143 (1967) and converted to the acid chloride using thionyl chloride.

Exemplary 3-coumaranol compounds useful herein include the 5-halo-(i.e., fluoro, chloro, bromo and iodo) 3-coumaranols, 5-nitro-3-coumaranol, 3-coumaranol, 5-methoxy-3-coumaranol, 5-butoxy-3-coumaranol, 5-decyl-3-coumaranol, 5-sulfonylmethyl-3-coumaranol, 5-thiomethyl-3-coumaranol and the like. 3-Coumaranol compounds preferred for use in the preparation of the compounds of this invention by virtue of their low cost, ease of preparation and the high insecticidal activity of the cyclopropanecarboxylic esters which they form include: 3-coumaranol, 5-methoxy-3-coumaranol, 5-chloro-3-coumaranol, 5-methyl-3-coumaranol and 5-nitro-3-coumaranol.

The compounds of this invention can exist in several isomeric and optically isomeric forms, e.g., cis-configuration, trans-configuration, dextro- and levorotatory forms of each, etc., and mixtures and racemates thereof. It is intended that the claims herein be construed to encompass all such forms and mixtures thereof. Preferred insecticidal esters herein are 3-coumaranyl chrysanthemate, 5-chloro-3-coumaranyl chrysanthemate, 5-nitro-3-coumaranyl chrysanthemate, 5-methoxy-3-coumaranyl chrysanthemate, 3-coumaranyl 2,2,3,3-tetramethylcyclopropanecarboxylate, 5-chloro-3- coumaranyl 2,2,3,3-tetramethylcyclopropane-carboxylate, 5-nitro-3-coumaranyl 2,2,3,3-tetramethylcyclopropanecarboxylate, 5-methoxy-3-coumaranyl 2,2,3,3-tetramethylcyclopropanecarboxylate, 3-coumaranyl3-(2,2-tetramethylene ethenyl)-2,2-dimethylcyclopropanecarboxylate, 5-chloro-3-coumaranyl 3-(2,2-tetramethylene ethenyl)-2,2-dimethylcyclopropanecarboxylate, 5-nitro-3-coumaranyl 3-(2,2-tetramethylene ethenyl)-2,2-dimethylcyclopropanecarboxylate, 5-methoxy-3-coumaranyl 3-(2,2-tetramethylene ethenyl)-2,2-dimethylcyclopropanecarboxylate, 5-phenyl-3-coumaranyl chrysanthemate, 5-benzyl-3-coumaranyl chrysanthemate, 5-phenyl-3-coumaranyl 2,2,3,3,-tetramethylcyclopropanecarboxylate, 5-benzyl-3-coumaranyl 2,2,3,3,-tetramethylcyclopropanecarboxylate, 5-phenyl-3-coumaranyl 3-(2,2-tetramethylene ethenyl)-2,2-dimethylcyclopropanecarboxylate and 5-benzyl-3-coumaranyl 3-(2,2-tetramethylene ethenyl)-2,2-dimethylcyclopropanecarboxylate.

The preparation of the coumaranyl cyclopropanecarboxylic acid esters of the present invention is described in more detail in the following examples. The inert organic solvents used in the procedures are those which do not react with the 3-coumaranyl compounds or with the cyclopropanecarboxylic acids or acid halides. Such solvents are preferably aprotic solvents such as hexane, benzene, acetone, ether, glyme, and the like. The examples are not intended to be limiting but only to demonstrate the preparation of a variety of compounds of this invention.

EXAMPLE I

Step 1. According to the precedure of Corey and Chaykovski, above, a nitrogen blanketed mixture of 2.52 g. (0.064 mol.) of sodium hydride (as a 61% mineral oil dispersion) and 14.1 g. (0.064 mol.) of trimethyloxosulfonium iodide was stirred and treated dropwise over 15 min. with 70 ml. of dry dimethyl sulfoxide. The reaction mixture was then cooled to 10° C and a solution of 7.32 g. (0.06 mol.) of salicylaldehyde in 30 ml. of dry dimethyl sulfoxide was added in one portion with stirring. After 5 min. the cooling bath was removed and stirring was continued at room temperature for 2 hours and at 50° C for 1 hour. The cooled reaction mixture was poured into ice water and the aqueous mixture extracted with ether. The combined ether extracts were washed twice with water, once with saturated salt solution, and dried over magnesium sulfate. Evaporation of the solvent at reduced pressure yielded 7.2 g. (88%) of 3-coumaranol).

Further purification by passing through a Florisil column afforded 5.87 g. of product: ir (neat) 2.98, 6.20, 6.23, 6.75, 8.1, 10.4, 13,2μ; nmr (CCl₄) τ 3.0 (multiplet, 4 hydrogens, aromatic), 5.0 (multiplet, 1 hydrogen, -CHOH), 5.81 (multiplet, 2 hydrogens, —CH₂—), 6.62 (singlet, 1 hydrogen, OH).

Step 2. A mixture of 11 g. (0.059 mol.) of (±)chrysanthemoyl chloride (mixture of cis- and trans-isomers) and 9.5 g. (0.12 mol.) of dry pyridine in 125 ml. of dry benzene was cooled to 0° C. A solution of 8.05 g. (0.059 mol.) of the 3-coumaranol prepared in the first step in 25 ml. of dry benzene was added with stirring over several minutes. The cooling bath was removed and the reaction mixture was stirred at room temperature for 24 hours. The reaction was added to saturated salt solution and the layers were separated. The aqueous layer was further extracted with ether and the combined organic layers were washed twice with 3% aqueous hydrochloric acid and several times with saturated salt solution prior to drying with magnesium sulfate. Evaporation of the solvent at reduced pressure gave 20 g. of crude ester product. This was purified by passing through a Florisil column to yield 14 g. (83%) of (±) cis,trans-3-coumaranyl chrysanthemate: ir(neat) 3.42, 5.79, 6.20, 6.23, 8.61, 13.2μ; nmr(CCl₄) τ 2.64-3.4 (multiplet, 4 hydrogens, aromatic) 3.92 (multiplet, 1 hydrogen,

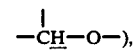

4.75, 5.26 [2 doublets, 1 hydrogen, J = 8 Hz, cis and trans (CH₃)₂C=CH—] 5.62 (multiplet, 2 hydrogens, —CH₂O—), 8.36 [singlet, 6 hydrogens, (CH₃)₂C=], 8.78, 8.90 [2 singlets,

$n_D^{25}$ 1.5271.

In the above procedure, the chrysanthemoyl chloride is replaced by an equivalent amount of 3-(2,2-tetramethylene ethenyl)-2,2-dimethylcyclopropanecarboxylic acid chloride and 2,2,3,3-tetramethylcyclopropanecarboxylic acid chloride, respectively, and the compounds 3-coumaranyl 3-(2,2-tetramethylene ethenyl)-2,2-dimethylcyclopropanecarboxylate and 3-coumaranyl 2,2,3,3-tetramethylcyclopropanecarboxylate are secured.

EXAMPLE II

In the same manner as described in Example I, Step 1, 1.26 g. (0.032 mol.) of sodium hydride (as a 61% mineral oil dispersion) and 7. g. (0.032 mol.) of trimethyloxosulfonium iodide in 35 ml. of dry dimethyl sulfoxide was treated with a solution of 4.68 g. (0.030 mol) of 5-chlorosalicylaldehyde in 15 ml. of dimethyl sulfoxide. Chromatographic purification gave 2.5 g. (49%) of 5-chloro-3-coumaranol: m.p. 85°–86° C; ir(CCl₄) 2.78, 2.94, 3.38, 6.2, 6.78, 10.3μ; nmr (CDCl₃) τ 2.5-3.4 (mutliplet, 3 hydrogens, aromatic), 4.92 (multiplet, 1 hydrogen, —CHOH), 5.76 (multiplet, 2 hydrogens, —CH₂—), 6.80 (singlet, 1 hydrogen, OH).

As described in Example I, Step 2, a solution of 2 g. (0.012 mol.) of 5 chloro-3-coumaranol in 8 ml. of dry benzene was allowed to react with a solution of 2.2 g. (0.012 mol.) of chrysanthemoyl chloride and 1.9 g. (0.024 mol.) of dry pyridine in 10 ml. of dry benzene to yield 2.33 g. (61%) of (±) cis,trans-5-chloro-3-coumaranyl chrysanthemate, a viscous liquid: ir(film) 3.42, 5.78, 6.2, 6.78, 8.62μ; nmr (CCl₄) τ 2.64-3.4 (multiplet, 3 hydrogens, aromatic), 3.9 (multiplet, 1 hydrogen,

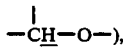

5.56 (multiplet, 2 hydrogens, —CH₂—), 8.36 [singlet, 6 hydrogens, (CH₃)₂C=], 8.74, 8.92 [2 singlets,

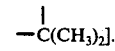

].

In the above procedure, the chrysanthemoyl chloride is replaced by an equivalent amount of 3-(2,2-tetramethylene ethenyl)-2,2-dimethylcyclopropanecarboxylic acid chloride and 2,2,3,3-tetramethylcyclopropanecarboxylic acid chloride, respectively, and the compounds 5-chloro-3-coumaranyl 3-(2,2-tetramethylene ethenyl)-2,2-dimethylcyclopropanecarboxylate and 5-chloro-3-coumaranyl 2,2,3,3-tetramethylcyclopropane-carboxylate are secured.

EXAMPLE III

In the same manner as described in Example I, Step 1, 1.26 g. (0.032 mol.) of sodium hydride (as a 61% mineral oil dispersion) and 7 g. (0.032 mol.) of trimethyloxosulfonium iodide in 35 ml. of dry dimethyl sulfoxide was treated with a solution of 4.56 g. (0.030 mol.) of 5-methoxysalicylaldehyde in 15 ml. of dimethyl sulfoxide. Chromatographic purification gave 1.6 g. (32%) of 5-methoxy-3-coumaranol: ir(neat) 2.98, 3.4, 6.73, 8.8, 9.74, 10.4μ; nmr (CCl$_4$) τ 2.3–3.5 (multiplet, aromatic) 4.92 (multiplet, —CHOH), 5.72 (multiplet, —CH$_2$—), 6.4 (singlet, —OCH$_3$), 7.2 (singlet, —OH).

As described in Example I, Step 2, a solution of 2 g. (0.012 mol.) of 5-methoxy-3-coumaranol in 8 ml. of dry benzene was allowed to react with a solution of 2.2 g (0.012 mol.) of chrysanthemoyl chloride and 1.9 g. (0.024 mol.) of dry pyridine in 10 ml. of dry benzene to yield 2.3 g. (61%) of (±) cis, trans- 5-methoxy-3-coumaranyl chrysanthemate as a viscous liquid: ir(neat) 3.39, 5.79, 6.18, 6.25, 6.78μ; nmr(CCl$_4$) τ 2.5–3.6 (multiplet, aromatic), 3.95 (multiplet, $$-\overset{|}{C}H-O-),$$

6.04 (multiplet, —CH$_2$—), 6.4 (singlet, —OCH$_3$), 8.4 [singlet, (CH$_3$)$_2$C=], 8.8, 8.95 [2 singlets, $$-\overset{|}{C}(\underline{C}H_3)_2].$$

In the above procedure, the chrysanthemoyl chloride is replaced by an equivalent amount of 3-(2,2-tetramethylene ethenyl)-2,2-dimethylcyclopropanecarboxylic acid chloride and 2,2,3,3-tetramethylcyclopropanecarboxylic acid chloride, respectively, and the compounds 5-methoxy-3-coumaranyl 3-(2,2-tetramethylene ethenyl)-2,2-dimethylcyclopropanecarboxylate and 5-methoxy-3-coumaranyl 2,2,3,3-tetramethylcyclopropanecarboxylalte are secured.

In the above procedure, the 5-methoxysalicylaldehyde is replaced by an equivalent amount of 5-nitrosalicylaldehyde and 5-nitro-3-coumaranyl is secured. Esterification of the 5-nitro-3-coumaranyl with the respective cyclopropanecarboxylic acid chlorides in the foregoing manner affords 5-nitro-3-coumaranyl chrysanthemate, 5-nitro-3-coumaranyl 3-(2,2-tetramethylene ethenyl)-2,2-dimethylcyclopropane carboxylate and 5-nitro-3-coumaranyl 2,2,3,3-tetramethylcyclopropanecarboxylate, respectively.

Additional compounds encompassed by the present invention can be prepared as in Example I by replacing the salicylaldehyde in Step 1 with 5-methylsalicylaldehyde, 5-ethylsalicylaldehyde, 5-phenylsalicylaldehyde and 5-benzylsalicylaldehyde, respectively. Esterification of the resulting 5-substituted-3-coumaranols with the foregoing cyclopropanecarboxylic acid halides yields 5-methyl-3-coumaranyl chrysanthemate; 5-ethyl-3-coumaranyl chrysanthemate; 5-methyl-3-coumaranyl 3-(2,2-tetramethylene ethenyl)-2,2-dimethylcyclopropane carboxylate; 5-ethyl-3-coumaranyl 3-(2,2-tetramethylene ethenyl)-2,2-dimethylcyclopropanecarboxylate; 5-methyl-3-coumaranyl 2,2,3,3-tetramethylcyclopropanecarboxylate; 5-ethyl-3-coumaranyl 2,2,3,3-tetramethylcyclopropanecarboxylate, and the 5-phenyl-3-coumaranyl- and 5-benzyl-3-coumaranylchrysanthemates, 2,2,3,3-tetramethylcyclopropanecarboxylates and 3-(2,2-tetramethylene ethenyl)-2,2-dimethylcyclopropanecarboxylates, respectively.

The outstanding insecticidal properties of the compounds of this invention can be seen from the following examples:

EXAMPLE VI

3-Coumaranyl chrysanthemate, 5-chloro-3-coumaranyl chrysanthemate, 5-methoxy-3-coumaranyl chrysanthemate, and natural pyrethrum, respectively, were dissolved in acetone and dispersed in distilled water with Triton X-100 emulsifier. The samples were applied for a 10 second period to houseflies retained in a 2 inches × 5 inches diameter screened cage. The spray is applied from the Water's vertical spray tower operating at 10 p.s.i. and discharging about 30 ml. of material per minute through an atomizer. The spray descends through an 8 inches stainless steel cylinder to test insects below the atomizer. The insects were retained in the sprayed cages for mortality observations. The results are set forth in Table 1 below.

TABLE 1

| Chrysanthemic Acid Ester | Housefly Mortality Tests % W/V | % Mortality (24 hr.) |
| --- | --- | --- |
| 3-coumaranol (Example I) | 0.0025 | 6 |
|  | 0.0025 + 0.025 PB* | 93 |
|  | 0.00125 | 5 |
|  | 0.00125 + 0.0125 PB* | 28 |
| 5-chloro-3-coumaranol (Example II) | 0.005 | 5 |
|  | 0.005 + 0.05 PB* | 99 |
|  | 0.0025 + 0.025 PB* | 56 |
| 5-methoxy-3-coumaranol (Example III) | 0.01 | 0 |
|  | 0.01 + 0.1 PB* | 100 |
|  | 0.005 + 0.05 PB* | 57 |
| Pyrethrum | 0.0025 | 20 |
|  | 0.0025 + 0.025 PB* | 96 |
|  | 0.00125 | 1 |
|  | 0.00125 + 0.0125 PB* | 46 |

*Piperonyl butoxide, an insecticidal synergist, has essentially no insecticidal activity at the concentrations reported above.

In the above test, the respective chrysanthemates are replaced by an equivalent amount of 3-coumaranyl 3-(2,2-tetramethylene ethenyl)-2-dimethylcyclopropanecarboxylate, 3-coumaranyl 2,2,3,3-tetramethylcyclopropanecarboxylate, 5-chloro-31 -coumaranyl 3-(2,2-tetramethylene ethenyl)-2,2-dimethylcyclopropanecarboxylate, 5-chloro-3-coumaranyl 2,2,3,3-tetramethylcyclopropanecarboxylate, 5-methoxy-3-coumaranyl 3-(2,2-tetramethylene ethenyl)-2,2-dimethylcyclopropanecarboxylate, 5-methoxy-3-coumaranyl 2,2,3,3-tetramethylcyclopropanecarboxylate, 5-nitro-3-coumaranyl chrysanthemate, 5-nitro-3-coumaranyl 3-(2,2-tetramethylene ethenyl)-2-dimethylcyclopropanecarboxylate, and 5-nitro-3-coumaranyl 2,2,3,3-tetramethylcyclopropanecarboxylate, respectively, and equivalent results are secured.

EXAMPLE V

3-Coumaranyl chrysanthemate and natural pyrethrum, respectively, were formulated in deodorized kerosene to give a deposit rate of 100 milligrams per square foot of area for residual evaluation against houseflies and 200 and 400 milligrams per square foot of area for residual evaluation against German cockroaches. The formulations were uniformly applied at the rate of 8 milliliters/sq.ft. on unpainted plywood and 3.5 milliliters/sq.ft. on vinyl asbestos with a camel hair brush. Adult insects were exposed to each treated panel for 1 hour (houseflies) or 2 hours (cockroaches), transferred to clean cages, and held for mortality counts. The same treated panels were used for re-exposures after the aging period indicated. The results were as follows:

TABLE 2

| Ester | Surface Type | Age of Residue (Days) | % Mortality (24 hr.) |
|---|---|---|---|
| Residual Activity Against Houseflies | | | |
| 3-coumaranol (Example I) | Plywood | 1 | 100 ( 9)* |
| | | 3 | 98 (21) |
| | | 7 | 83 ( 0) |
| | Vinyl | 1 | 100 (68) |
| | | 3 | 100 (11 0) |
| | | 7 | 59 (11 0) |

| Ester | Surface Type | Milligrams per sq. ft. | Age of Residue (Days) | % Mortality (48 hrs.) |
|---|---|---|---|---|
| Residual Activity Against Cockroaches | | | | |
| 3-coumaranol (Example I) | Plywood | 400 | 1 | 83 (100)* |
| | | | 3 | 83 (100) |
| | | | 7 | 90 (100) |
| | | | 14 | 73 ( 85) |
| | | 200 | 1 | 85 (100) |
| | | | 3 | 83 (100) |
| | | | 7 | 93 ( 95) |
| | | | 14 | 85 ( 65) |
| | Vinyl | 400 | 1 | 100 (100) |
| | | | 3 | 100 (100) |
| | | | 7 | 100 (100) |
| | | | 14 | 83 (100) |
| | | 200 | 1 | 100 (100) |
| | | | 3 | 95 (100) |
| | | | 7 | 70 (100) |
| | | | 14 | 20 ( 65) |

*The values set forth in parentheses are those secured for pyrethrum which serves as a positive control.

In the above procedure, the 3-coumaranyl chrysanthemate is replaced by an equivalent amount of the 5-ethyl-3-coumaranyl-, 5-methoxy-3-coumaranyl-, 5-bromo-3-coumaranyl-, 5-thiomethyl-3-coumaranyl-, 5-nitro-3-coumaranyl-, 5-sulfonylmethyl-2-coumaranyl-, 5-propoxy-3-coumaranyl-, 5-butoxy-3-coumaranyl-, 5-benzyl-3-coumaranyl-, and 5-phenyl-3-coumaranyl-esters of chrysanthemic acid, 3-(2,2-tetramethylene ethenyl)-2,2-dimethylcyclopropanecarboxylic acid, and 2,2,3,3-tetramethylcyclopropanecarboxylic acid, respectively, and equivalent results are secured.

EXAMPLE VI

3-Coumaranyl chrysanthemate has also been shown to be effective against 11 other insects as follows. All test species except the webbing clothes moth larvae were sprayed in the Water's vertical spray tower as described in Example IV. For the fabric tests, a two inch square area of wool fabric was dipped in the test formulations. The results secured with various insects are set forth below.

TABLE 3

Insect Mortality Tests

| Insect | Test compound + synergist* (% W/V) | Pyrethrum + synergist* (% W/V) | % Mortality (days) |
|---|---|---|---|
| Southern Armyworm | 0.05 + 0.2 | | 70 (2) |
| | | 0.05 + 0.2 | 100 (2) |
| Mexican Bean Beetle | 0.005 + 0.02 | | 80 (2) |
| | | 0.005 + 0.02 | 30 (2) |
| Pea Aphid | 0.005 + 0.02 | | 65 (2) |
| | | 0.005 + 0.02 | 100 (2) |
| Mite | 0.05 + 0.2 | | 69 (5) |
| | | 0.05 + 0.2 | 100 (5) |
| German Cockroach | 0.05 + 0.2 | | 30 (2) |
| | | 0.05 + 0.2 | 85 (2) |
| Adult mosquito | 0.05 + 0.2 | | 100 (1) |
| | | 0.05 + 0.2 | 100 (1) |
| Adult stable flies | 0.05 + 0.2 | | 100 (1) |
| | | 0.05 + 0.2 | 100 (1) |
| Black carpet beetle larvae | 0.05 + 0.2 | | 40 (7) |
| | | 0.05 + 0.2 | 40 (7) |
| Webbing clothes moth larvae | 0.05 + 0.2 | | 100 (7) |
| | | 0.05 + 0.2 | 100 (7) |
| Adult rice weevils | 0.05 + 0.2 | | 100 (3) |
| | | 0.05 + 0.2 | 100 (3) |
| Adult saw toothed grain beetles | 0.05 + 0.2 | | 100 (3) |
| | | 0.05 + 0.2 | 100 (3) |

*Synergist - Piperonyl butoxide

In the above procedure, the 3-coumaranyl chrysanthemate is replaced by an equivalent amount of the 5-ethyl-3-coumaranyl-, 5-methoxy-3-coumaranyl-, 5-bromo-3-coumaranyl-, 5-thiomethyl-3-coumaranyl, 5-nitro-3-coumaranyl-, 5-sulfonylmethyl-3-coumaranyl-, 5-propoxy-3-coumaranyl-, and 5-butoxy-3-coumaranyl-esters of 3-(2,2-tetramethylene ethenyl)-2,2-dimethylcyclopropanecarboxylic acid and 2,2,3,3-tetramethylcyclopropanecarboxylic acid, and the 5-ethyl-3-coumaranyl-, 5-methoxy-3-coumaranyl-, 5-bromo-3-coumaranyl-, 5-thiomethyl-3-coumaranyl-, 5-nitro-3-coumaranyl-, 5-sulfonylmethyl-3-coumaranyl-, 5-propoxy-3-coumaranyl-, and 5-butoxy-3-coumaranyl- esters of chrysanthemic acid, respectively, and equivalent results are secured.

As can be seen from the foregoing examples, representative compounds of this invention possess excellent insecticidal properties, comparing favorably with pyrethrum in most aspects and surpassing it in residual effect. Additionally, the esters herein are less toxic to mammals than pyrethrum as can be seen by the $LD_{50}$ values of one of the typical esters herein.

| Compound | $LD_{50}$ (rat) |
|---|---|
| 3-coumaranyl chrysanthemate | >7.57 g./kg. |
| Pyrethrum | 2.3 g./kg. |

The other esters herein are also less toxic than their corresponding pyrethrum analogs.

Insecticidal compositions containing the esters of the present invention can be formulated and utilized as oil solutions, emulsifiable concentrates, wettable powders, dusts, aerosols, or impregnated into wood, fabrics, etc., and provide a long lasting residual effect. Such compositions can include the generally employed carriers or diluents and auxiliary agents which are well-known to those skilled in the art. For example, suitable dusts can be prepared by admixing the compounds of the invention with dry free-flowing powders such as clay, bentonite, fuller's earth, diatomaceous earth, pyrophyllite, attapulgite, calcium carbonate, chalk or the like. The active compounds of the invention normally comprise up to about 10% by weight of such dust formulations.

An amount of up to about 3% is preferred and is suitable for most applications.

Likewise, suspensions of dispersions of the compounds in a non-solvent, such as water, can be suitably employed for the treatment of foilage. Also suitably employed are solutions of the insecticides of this invention in oil which is emulsified in water. Examples of oil solvents include hydrocarbons such as benzene and toluene, halogenated hydrocarbons such as chlorobenzene, chloroform, fluorotrichloromethane and dichlorodifluoromethane, and commercial mixtures of hydrocarbons such as the common Stoddard solvent, petroleum ethers, and the like.

Aerosols can be prepared by dissolving the compounds of the invention in a highly volatile liquid carrier such as trifluorochloromethane, nitromethane, dichlorodifluoroethane and the like, or by dissolving such compounds in a less volatile solvent, such as benzene or kerosene, and admixing the resulting solution with a highly volatile liquid aerosol carrier such as the polyfluorohydrocarbons commonly used as aerosol propellants.

The insecticidal esters of this invention are useful for destroying a variety of insects. Accordingly, a method aspect of the present invention comprises combating insects by applying to said insects, or to an insect habitat, an insecticidal amount of one or more of the novel compounds disclosed herein.

Preferably the esters of this invention are employed in combination with a synergistic agent, for example, piperonyl butoxide, piperonyl sulfoxide, β-butoxy-2'-thiocyanodiethyl ether and the like.

What is claimed is:

1. A method for combatting insects comprising applying to said insects, or to an insect habitat, an insecticidal amount of cyclopropanecarboxylic acid ester of the formula

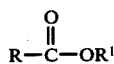

wherein R is a cyclopropane moiety selected from the group consisting of

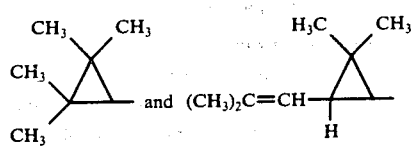

and wherein $R^1$ is a 3-coumaranyl moiety of the formula

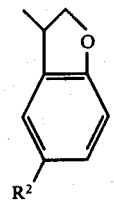

wherein $R^2$ is selected from the group consisting of hydrogen, halogen, nitro, thiomethyl, alkyl, alkoxyl, sulfonylmethyl, phenyl and benzyl.

2. The method according to claim 1 wherein the cyclopropanecarboxylic acid ester is a member selected from the group consisting of 3-coumaranyl chrysanthemate, 5-chloro-3-coumaranyl chrysanthemate, 5-nitro-3-coumaranyl chrysanthemate, 5-methoxy-3-coumaranyl chrysanthemate, 3-coumaranyl 2,2,3,3-tetramethylcyclopropanecarboxylate, 5-chloro-3-coumaranyl 2,2,3,3-tetramethylcyclopropanecarboxylate, 5-nitro-3-coumaranyl 2,2,3,3-tetramethylcyclopropanecarboxylate, 5-methoxy-3-coumaranyl 2,2,3,3-tetramethylcyclopropanecarboxylate, 5-phenyl-3-coumaranyl chrysanthemate, 5-benzyl-3-coumaranyl chrysanthemate, 5-phenyl-3-coumaranyl 2,2,3,3-tetramethylcyclopropanecarboxylate, and 5-benzyl-3-coumaranyl 2,2,3,3-tetramethylcyclopropanecarboxylate.

3. The method of claim 2 wherein the cyclopropanecarboxylic acid ester is 3-coumaranyl chrysanthemate.

4. The method of claim 2 wherein the cyclpopropanecarboxylic acid ester is 5-chloro-3-coumaranyl chrysanthemate.

5. The method of claim 2 wherein the cyclopropanecarboxylic acid ester is 5-methoxy-3-coumaranyl chrysanthemate.

* * * * *

UNITED STATES PATENT AND TRADEMARK OFFICE
CERTIFICATE OF CORRECTION

PATENT NO. : 4,053,629
DATED : Oct. 11, 1977
INVENTOR(S) : Wayne I. Fanta

It is certified that error appears in the above-identified patent and that said Letters Patent are hereby corrected as shown below:

Col. 1, line 39, after "and" and before "number" insert -- a --.

Col. 4, line 13, "cyclopropanecarboxyic" should be

-- cyclopropanecarboxylic --.

Col. 6, lines 44 & 45, "mutliplet" should be -- multiplet --.

Col. 8, line 57, "5-chloro-31 -coumaranyl 3-" should be

-- 5-chloro-3-coumaranyl 3- --.

Col. 9, Table 2, under "% Mortality (24 hr.)", line 26, "100 (11 0)" should be -- 100 (0) -- and line 27, "59 (11 0)" should be -- 59 (0) --.

Signed and Sealed this

Thirteenth Day of June 1978

[SEAL]

Attest:

RUTH C. MASON
Attesting Officer

DONALD W. BANNER
Commissioner of Patents and Trademarks